(12) United States Patent
Prien et al.

(10) Patent No.: US 9,198,701 B2
(45) Date of Patent: Dec. 1, 2015

(54) BONE FASTENER AND METHOD OF MANUFACTURING THE SAME

(75) Inventors: Ole Prien, Kiel (DE); Stefan Voelzow, Moenkeberg (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 13/993,744

(22) PCT Filed: Dec. 17, 2010

(86) PCT No.: PCT/EP2010/007748
§ 371 (c)(1),
(2), (4) Date: Aug. 15, 2013

(87) PCT Pub. No.: WO2012/079610
PCT Pub. Date: Jun. 21, 2012

(65) Prior Publication Data
US 2013/0325010 A1 Dec. 5, 2013

(51) Int. Cl.
*A61B 17/56* (2006.01)
*A61B 17/72* (2006.01)
*A61B 17/86* (2006.01)
*A61B 17/00* (2006.01)

(52) U.S. Cl.
CPC ........... *A61B 17/725* (2013.01); *A61B 17/7216* (2013.01); *A61B 17/863* (2013.01); *A61B 17/866* (2013.01); *A61B 17/72* (2013.01); *A61B 2017/00526* (2013.01)

(58) Field of Classification Search
CPC .... A61B 17/72; A61B 17/7233; A61B 17/84; A61B 17/846; A61B 17/88; A61B 17/744; A61B 17/1725

USPC .............. 606/321, 62–64; 411/411–413
See application file for complete search history.

(56) References Cited

U.S. PATENT DOCUMENTS

| 4,776,330 | A | | 10/1988 | Chapman et al. |
| 4,875,475 | A | | 10/1989 | Comte et al. |
| 5,735,653 | A | * | 4/1998 | Schiefer et al. ................. 411/82 |
| 6,030,162 | A | * | 2/2000 | Huebner ........................ 411/413 |
| 6,355,043 | B1 | | 3/2002 | Adam |
| 6,508,820 | B2 | | 1/2003 | Bales |
| 7,246,979 | B2 | * | 7/2007 | Fujii et al. ..................... 411/310 |

(Continued)

FOREIGN PATENT DOCUMENTS

| CH | 687229 A5 | 10/1996 |
| EP | 0829233 A1 | 3/1998 |

(Continued)

OTHER PUBLICATIONS

International Search Report for Application No. PCT/EP2010/007748 dated Jul. 4, 2011.

*Primary Examiner* — Jerry Cumberledge
*Assistant Examiner* — Tessa Matthews
(74) *Attorney, Agent, or Firm* — Lerner, David, Littenberg, Krumholz & Mentlik, LLP

(57) ABSTRACT

A bone fastener for use in orthopaedic surgery for anchoring an intramedullary nail to bone has a shaft with a front region and a rear region adjacent to the front region. The rear region has one or more explantation grooves helically arranged for facilitating the explantation of the bone fastener. Two axially spaced apart grooves or groove sections are separated by a flat shaft portion defining an outside diameter of the rear region, wherein the rear region has a core diameter greater than a core diameter of the front region.

18 Claims, 4 Drawing Sheets

(56) References Cited

U.S. PATENT DOCUMENTS

| | | |
|---|---|---|
| 7,423,235 B2 * | 9/2008 | Severance, Jr. .......... 219/121.59 |
| 2002/0057954 A1 * | 5/2002 | Kato ............................ 411/386 |
| 2006/0036248 A1 * | 2/2006 | Ferrante et al. ................. 606/64 |
| 2006/0095040 A1 * | 5/2006 | Schlienger et al. ............. 606/73 |
| 2009/0024174 A1 * | 1/2009 | Stark ............................ 606/321 |
| 2010/0036433 A1 | 2/2010 | Jackson |
| 2010/0249852 A1 * | 9/2010 | Brumfield et al. ............. 606/282 |
| 2012/0203226 A1 * | 8/2012 | Schlienger et al. ............. 606/64 |
| 2013/0220636 A1 * | 8/2013 | Drenth et al. ................. 166/380 |

FOREIGN PATENT DOCUMENTS

| | | |
|---|---|---|
| EP | 1260188 A1 | 11/2002 |
| WO | 2004086991 A1 | 10/2004 |
| WO | 2006007553 A2 | 1/2006 |
| WO | 2006029274 A1 | 3/2006 |

\* cited by examiner

BONE FASTENER AND METHOD OF MANUFACTURING THE SAME

CROSS-REFERENCE TO RELATED APPLICATION

The present application is a national phase entry under 35 U.S.C. §371 of International Application No. PCT/EP2010/007748 filed Dec. 17, 2010, published in English, incorporated herein by reference.

TECHNICAL FIELD

The present disclosure generally relates to a bone fastener for use in orthopaedic surgery that may be used for fixing an implant such as an intramedullary nail to bone. The disclosure further relates to an implant system for fixation of bone, and to a manufacturing method for such a bone fastener.

BACKGROUND

Bone fasteners are typically bone screws or pegs which are inserted into bone. Basically, bone screws are used in two different ways: in a first application bone screws serve to fix bone or bone fragments in a desired position relative to one another. In this case the bone screw is used alone. In a second application the bone screw is used as a compression screw or a locking screw in order to position additional elements as fixation elements in or on bone. Here, bone screws are used, for example, together with intramedullary nails (marrow nails). Another area of application is osteosynthesis, in which a biocompatible element substitutes for a bone or a bone fragment. For example, a bone plate can be anchored by bone screws to bone.

Bone screws are available in a plurality of variations for different applications. For example, U.S. Pat. No. 6,030,162 A relates to a compression bone screw for creating an axial tension along its length. The screw has a screw thread formed thereon in a leading section and a trailing section with a threaded or an unthreaded section therebetween. The core diameter as well as the outside diameter of the thread varies over the entire length of the bone screw.

U.S. Pat. No. 6,355,043 B1 relates to a bone screw for anchoring a marrow nail. The bone screw includes a head part, a middle part, and a distal part. A thread extends from a proximal portion of the head part to the distal part, at a constant core diameter over the entire length. The proximal portion of the head part includes a proximal thread having an outer diameter which is greater than the outer diameter of the middle and distal part and greater than an inner diameter of a transverse bore in the marrow nail.

U.S. Pat. No. 4,875,475 and EP 1 260 188 A1 relate to a bone screw for insertion into bores of an intramedullary nail. The bone screw has a head and a shaft attached thereto. The shaft includes a front region and a rear region. The front region has a thread for anchoring the intramedullary nail to bone. The rear region of the shaft is unthreaded and has a smooth outer peripheral surface. The smooth rear region of the shaft is positioned within a transverse bore in the intramedullary nail for supporting the nail.

The conventional bone screws for anchoring an intramedullary nail to bone have several drawbacks. A bone screw with a continuous thread along its entire shaft has a low endurance limit. Since such a bone screw has a low strength, a greater diameter is often desirable. Moreover, a bone screw with a shaft having a thread over the full length of the shaft can only be used to fix an intramedullary nail to bone. However, such a bone screw may not be appropriate to interact with the intramedullary nail for compressing aligned bone pieces. Typically, bone screws for supporting an intramedullary nail include a shaft having a threaded front region and an unthreaded smooth rear region. Once the intramedullary nail is implanted, the smooth shaft of such bone screws is arranged within a transverse bore of the intramedullary nail. The side wall edges of the transverse bore in the nail or an adjusting means abuts against the smooth shaft region of the bone screw for supporting the nail and adjusting force to act between aligned bone pieces for holding them together. However, bone screws with a smooth unthreaded shaft portion can only be removed (explanted) by a self-retaining screw driver. Moreover, due to the smooth shaft surface, such screws can get stuck within the transverse bore of the intramedullary nail or within the bone, whereby the explantation is extremely hindered.

SUMMARY

Aspects of the present disclosure are directed to facilitating the explantation of bone fasteners anchoring an intramedullary nail to bone, and to provide a bone fastener which is suitable for locking and compression interaction with an intramedullary nail.

According to a first aspect, there is provided a bone fastener for use in orthopaedic surgery for anchoring an intramedullary nail to bone, wherein the bone fastener has a shaft with a front region and a rear region. The front region has an anchoring thread for attaching the bone fastener to bone, wherein the front region has first core diameter and the anchoring thread has a thread pitch. The rear region has one or more explantation grooves helically arranged at a pitch substantially corresponding to the pitch of the anchoring thread for facilitating explantation of the bone fastener. Further, two axially spaced apart grooves or groove sections are separated by a flat shaft portion defining an outside diameter of the rear region, wherein the rear region has a second core diameter greater than the first core diameter.

In the aspect described above, the explantation groove may be defined by a continuous explantation thread. The explantation thread can have thread peaks defining the flat shaft portion. The thread peaks may thus have an essentially planar top portion.

The rear region may comprise multiple separate explantation grooves which are arranged in the manner of a discontinuous thread. The distance between the multiple separate grooves can be between 0.1 and 10.0 mm, in particular between 1.0 mm and 5.0 mm. Further, the multiple separate grooves can be uniformly distributed along the rear region of the shaft. In one possible implementation, a first groove section may be arranged in the rear region adjacent to the front region, and another groove section may be arranged in the rear region adjacent to a head of the bone fastener, such that there is a distance therebetween. Alternatively, or additionally, a groove section may be arranged in the central area of the rear region.

The thread in the rear region can be formed as a flat, square or a trapezoidal thread. The anchoring thread in the front region may be formed as a cortical thread, a spongiosa thread or a cancellous thread. Further, the front region may have a tip, and the thread in the front region may run out in the tip.

The thread in the rear region as well as the thread in the front region may have a constant thread pitch. Both, the thread pitch of the thread in the rear region and the thread pitch of the anchoring thread in the front region may range between 0.1 mm and 5.0 mm, in particular between 1.0 mm and 4.0 mm (e.g., between 0.25 mm and 3.0 mm). Further, each of the threads may be a multiple thread such as a double or triple thread.

In one implementation, the outside diameter in the flat shaft portion of the rear region may approximately equal an outside diameter of the anchoring thread. Both outside diameters can range between 1.0 mm and 10.0 mm, in particular between 2.0 mm and 8.0 mm (e.g., between 3.0 mm and 5.0 mm). Further, the first core diameter of the shaft in the front region can be constant. Additionally, or alternatively, the second core diameter of the shaft in the rear region may be constant. The first core diameter as well as the second core diameter of the shaft may range between 0.5 mm and 10.0 mm, in particular between 1.0 mm and 8.0 mm (e.g., between 2.0 mm and 5.0 mm).

The one or more explantation grooves may have a groove width smaller than a width of the flat shaft portion in axial direction. The width of the flat shaft portion may be between two and four times the groove width. Moreover, the width of the flat shaft portion may be between 1.0 mm and 10.0 mm, in particular between 2.0 mm and 6.0 mm (e.g., between 3.0 mm and 5.0 mm). Moreover, the one or more explantation grooves can have a depth in radial direction smaller than a thread depth of the anchoring thread. The depth of the one or more explantation grooves may range between 0.1 and 0.3 times the thread depth of the anchoring thread. The depth (or thread depth) of the one or more explantation grooves can range between 0.1 mm and 3.0 mm, in particular between 0.15 mm and 1.5 mm. The thread depth of the anchoring thread can be between 0.2 mm and 5.0 mm, in particular between 0.3 mm and 4.0 mm.

In one implementation, the shaft can include a transition region between the front region and the rear region. The transition region may, for example, comprise mutually adjoining parts of the front region and the rear region. Thus, the explantation groove as well as the anchoring thread may run out in the transition region. Further, the explantation groove and the anchoring thread can overlap in the transition region. In an alternative implementation, the transition region my be unthreaded.

The bone fastener may have a head attached to the shaft. The head may have a diameter which is approximately between 1.0 mm and 20.0 mm. Further, the outer diameter of the head can be the same as or greater than the outer diameter of the shaft. The overall length of the bone fastener can be between 10 mm and 200 mm, for example between 30 mm and 100 mm. A length of the shaft may be between 10 mm and 200 mm. Further, the rear region may have a length between 10 mm and 200 mm, and the front region may have a length between 5 mm and 200 mm.

According to a further aspect, there is provided an implant system for use in orthopaedic surgery for fixation of bone. The implant system comprises an intramedullary nail having at least one transverse bore and at least one bone fastener for anchoring the intramedullary nail to bone. The at least one bone fastener has a shaft including a front region to penetrate the intramedullary nail through the at least one transverse bore, and a rear region to support the intramedullary nail at the at least one transverse bore. The front region has a first core diameter and an anchoring thread for attaching the bone fastener to bone, and the anchoring thread has a thread pitch. The rear region has one or more explantation grooves helically arranged at a pitch substantially corresponding to the pitch of the anchoring thread for facilitating explantation of the bone fastener, wherein two axially spaced apart grooves or groove sections are separated by a flat shaft portion defining an outside diameter of the rear region and wherein the rear region has a second core diameter greater than the first core diameter.

In the aspect described above, the one or more explantation grooves of the rear region may be configured to guide, upon an explantation of the at least one bone fastener, the at least one bone fastener inserted in the at least one transverse bore out of the at least one transverse bore. For this purpose, the explantation grooves may be configured to cooperate with, for example, perimetral portions of the transverse bore or other portions of the nail upon explantation.

The intramedullary nail can have at least one hollow portion and an adjusting member within said hollow portion. The at least one transverse bore may be formed as an elongated hole in the at least one hollow portion, wherein the adjusting member can be configured to apply a force axially of the intramedullary nail to the at least one bone fastener inserted in the elongated hole. Alternatively, the at least one transverse bore can be a circular hole.

According to a further aspect, there is provided a method of manufacturing a bone fastener having a shaft with a front region and a rear region. The front region includes an anchoring thread for attaching the bone fastener to bone, wherein the front region has a first core diameter and the anchoring thread has a thread pitch. The rear region has one or more explantation grooves for facilitating explantation of the bone fastener. The method comprises the step of guiding a milling tool for producing the anchoring thread in the front region and the one or more explantation grooves in the rear region in such a way that the one or more explantation grooves are helically arranged at a pitch substantially corresponding to the pitch of the anchoring thread and two axially spaced apart grooves or groove sections are separated by a flat shaft portion defining an outside diameter of the rear region, and that the rear region has a second core diameter greater than the first core diameter. Due to the fact that the rear region of the shaft includes one or more helically arranged explantation grooves, the explantation of the bone fastener out of bone and out of a transverse bore of an intramedullary nail is facilitated. In particular, the explantation grooves support an easy screwing-out of the bone fastener without getting stuck.

BRIEF DESCRIPTION OF THE DRAWINGS

These and other features, aspects and advantages of the present disclosure will become apparent from the following detailed description taken in conjunction with the accompanying drawings, wherein.

DETAILED DESCRIPTION

Figure 1:
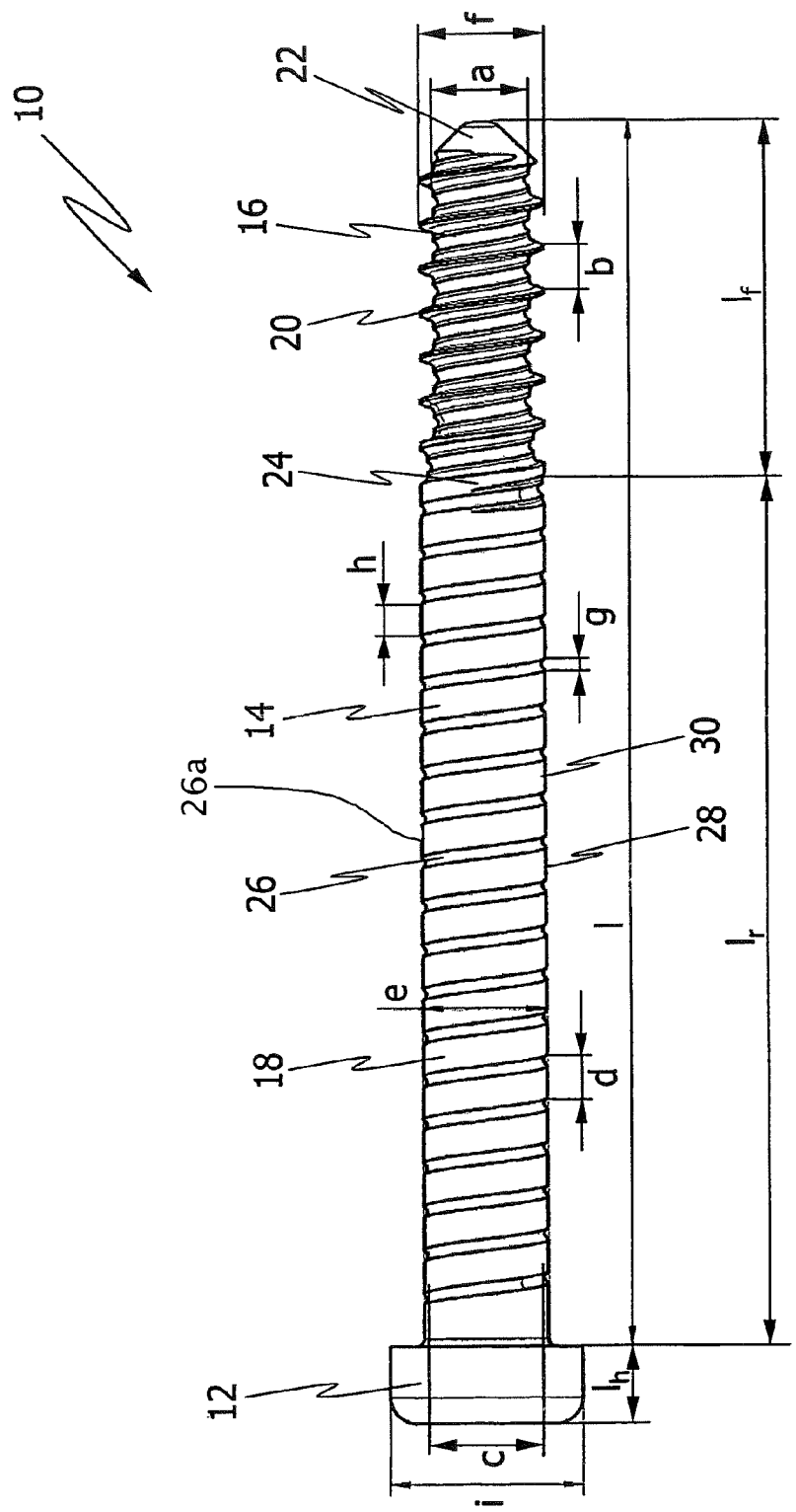
FIG. 1 is a side view of a bone fastener embodiment.

Referring to FIG. 1, there is shown a side view of an embodiment of a bone fastener in the form of a bone screw 10 for use in orthopaedic surgery for anchoring an intermetrolarly nail (not shown in FIG. 1) to bone. The bone screw 10 comprises a head 12 and a shaft 14 attached thereto. The shaft 14 includes a front region 16 and a rear region 18. The front region 16 has an anchoring thread 20 for attaching the bone screw 10 to bone. It can be seen from FIG. 1 that the anchoring thread 20 is a cortical thread 20 having an essentially constant core diameter along the shaft 14 in the front region 16. Further, the cortical thread 20 of the front region 16 has a thread pitch b.

As shown in FIG. 1, the front region includes a tip 22, and the cortical thread 20 runs out in the tip 22. The tip 22 has the form of a truncated cone. On the other end of the front region, the cortical thread 20 runs out into a transition region 24 comprising mutually ajoining parts of the front region 16 and the rear region 18. In an alternative embodiment, the transition region 24 could also be configured as a smooth (e.g., unthreaded) shaft portion.

As illustrated in FIG. 1, the rear region 18 of the shaft 14 is adjacent to the front region 16 and has explantation grooves 26 helically arranged at a pitch d corresponding to the pitch b of the cortical thread 20 of the front region 16. The axially spaced apart grooves 26 or groove sections 26 are separated by a flat shaft portion 28 defining an outside diameter e of the rear region 18. In the case of the bone screw 10, the outside diameter e of shaft 14 is constant. Generally, the outside diameter e of the rear region 18 is substantially equal to an outside diameter f of the front region 16. Thus, the outside diameter e in the flat shaft portion 28 of the rear region 18 approximately equals the outside diameter f of the cortical thread 20.

As also illustrated in FIG. 1, the rear region 18 has a core diameter c greater than the core diameter a of the front region. Further, the core diameter c of the shaft 14 in the rear region 18 is also constant. In an alternative embodiment, the core diameters a and c could be varying.

As further shown in FIG. 1, the explantation groove 26 is defined by a continuous explantation thread 26a which has thread peaks 30 defining the flat shaft portion 28. Alternatively, the rear region 18 may comprise multiple separate grooves 26 which are arranged in the manner of a discontinuous thread (not shown in FIG. 1). The thread 26a of the rear region 18 is formed as a flat trapezoidal thread 26a. Further, the explanatation groove 26 has a groove width g which is smaller than a width h of the flat shaft portion 28 in axial direction of the shaft 14. As shown in FIG. 1, the explantation groove 26 has a depth in radial direction smaller than a thread depth of the anchoring thread 20 of the front region 16.

The head 12 of bone screw 10 is thread-free and has an enlarged diameter i in relation to the outside diameter e of the rear region 18 and the outside diameter f of the front region 16. The diameter i of the head 12 is approximately 5.0 mm. Further, the head 12 has a length $l_h$ of approximately 3.0 mm. The head 12 is further configured with a recess for receiving a screw driver or a wrench (e.g., in the form of a hexalobular internal driving feature).

The overall length of the bone screw 10 is approximately 50 mm. The overall length of bone screw 10 is defined by the length $l_h$ of head 12 and the length l of the shaft 14. The length l of shaft 14 amount to 47 mm. Further, the length l of the shaft 14 can be divided into the length $l_r$ of the rear region 18 and the length $l_f$ of the front region 16. The length $l_r$ of the rear region 18 is approximately 32 mm, and the length $l_f$ of the front region 16 is approximately 15 mm.

Figure 2:
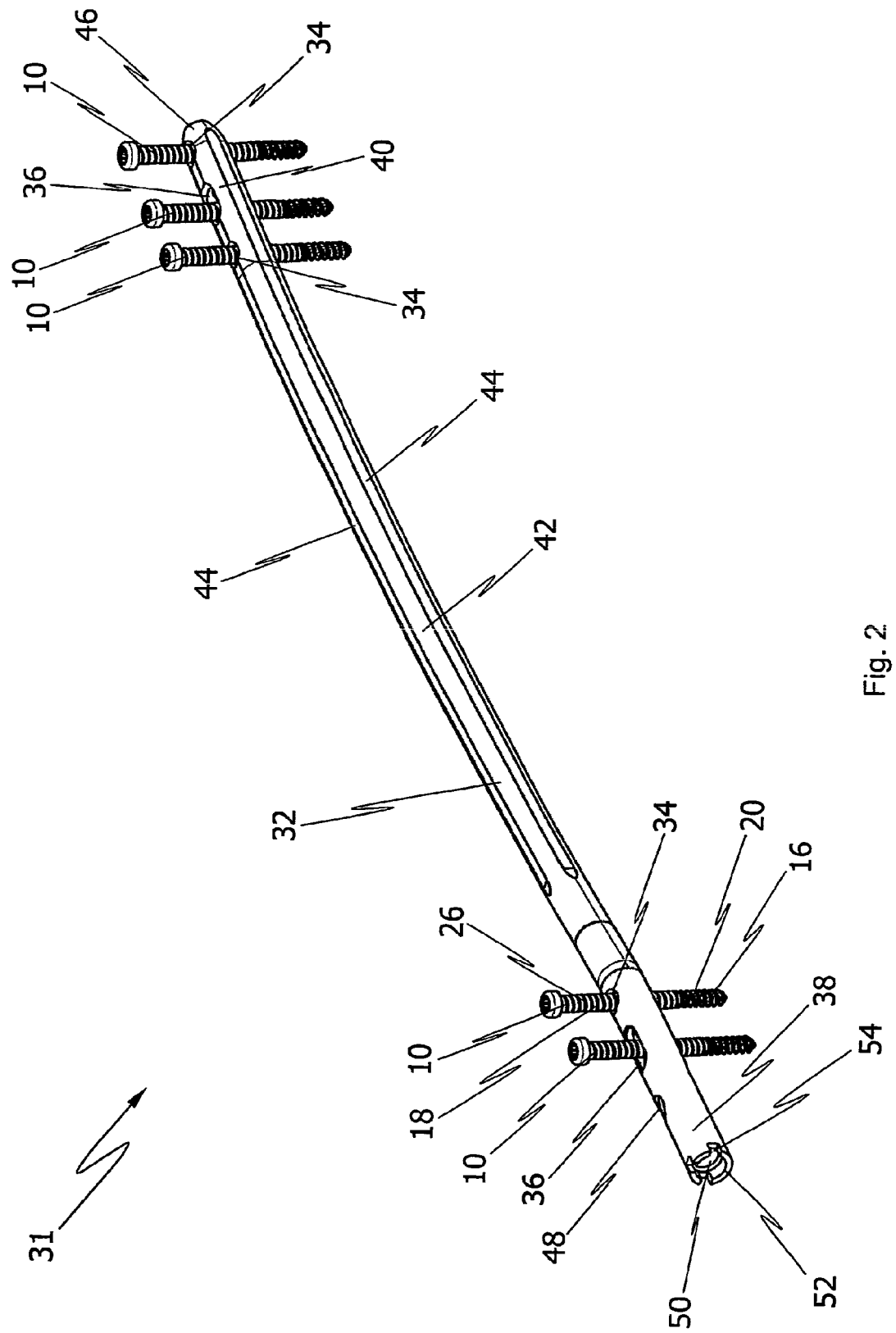
FIG. 2 is a perspective view of a dummy implant system embodiment.
Figure 3:
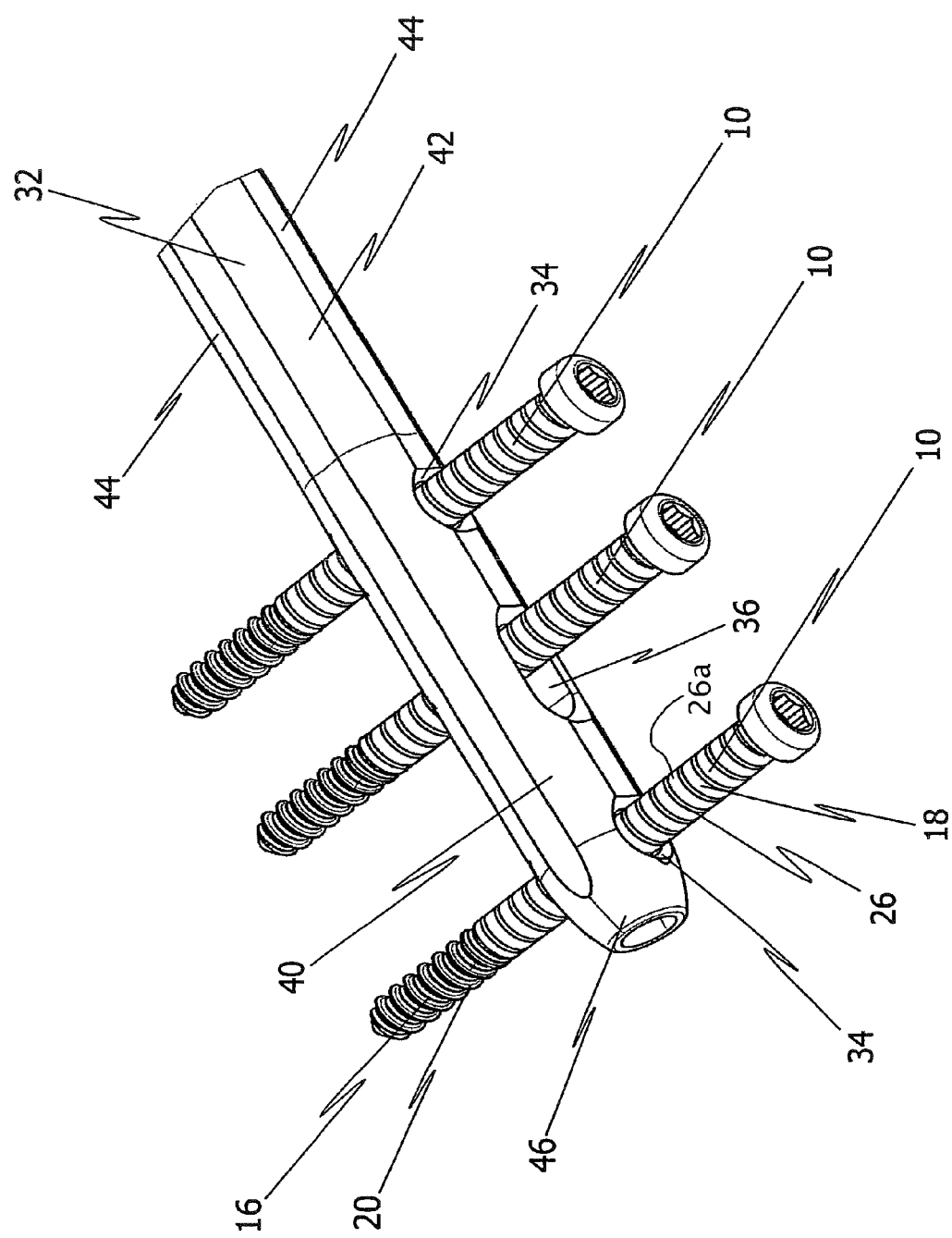
FIG. 3 is a detailed view of a distal end portion of the dummy implant system shown in FIG. 2.
Figure 4:
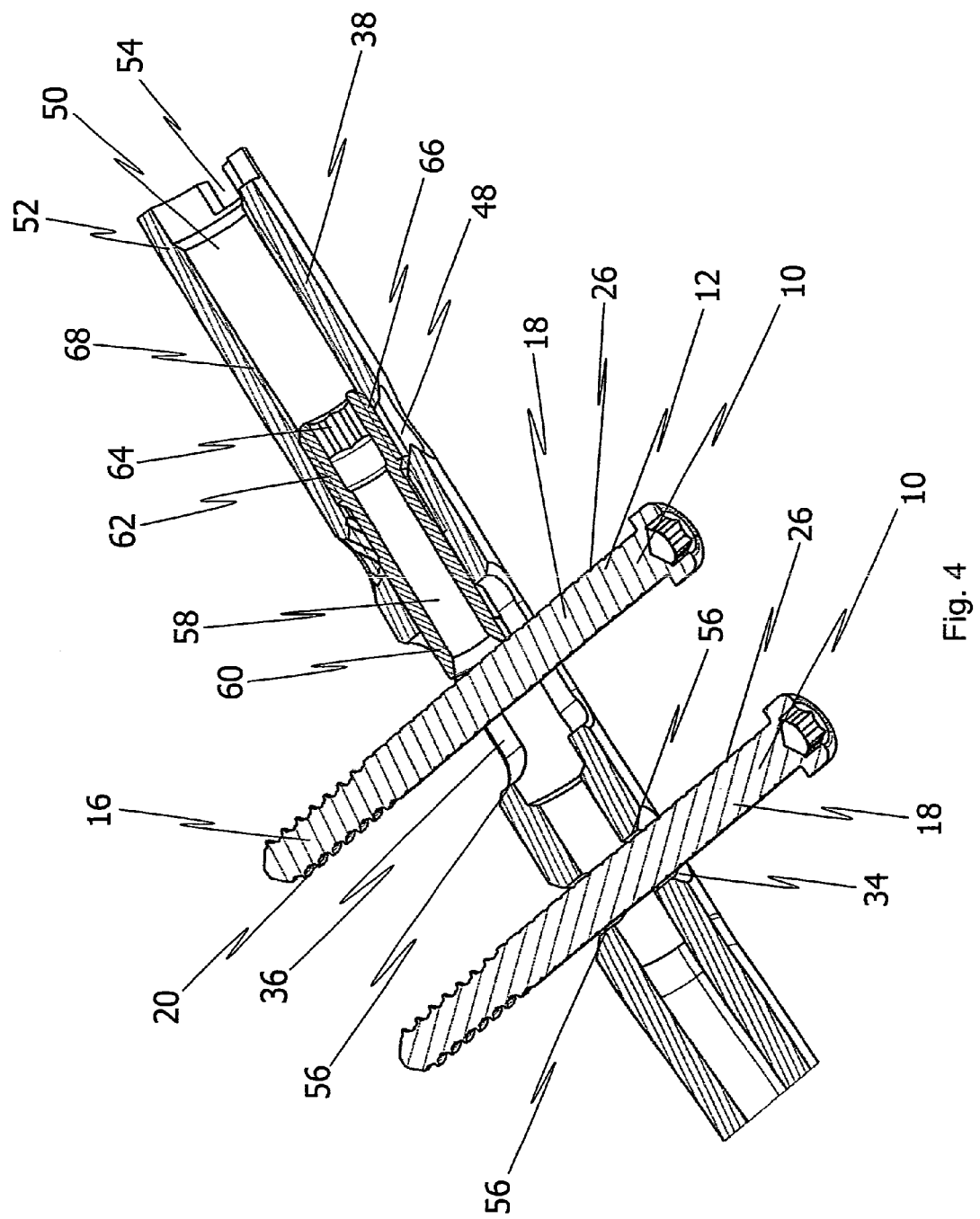
FIG. 4 is a cross-sectional view of a proximal end portion of the dummy implant system shown in FIG. 2.

FIGS. 2 to 4 show an embodiment of a dummy implant system 31 having a dummy implant 32 for use in orthopaedic surgery for fixation of the bone and multiple bone screws 10 as depicted in FIG. 1.

FIG. 2 illustrates a perspective view of the dummy implant system 31 with the dummy implant in the form of a dummy intramedullary nail 32. The dummy intramedullary nail 32 can be adapted as needed (e.g., in terms of shape, thickness, length, diameter, etc.) for use in orthopaedic surgery for fixation of bone. The intramedullary nail 32 has several transverse bores 34, 36, such as circular holes 34 and elongated holes 36. Further, as shown in FIG. 2, the intramedullary nail 32 has a proximal end portion 38 and a distal end portion 40 with an elongated shaft portion 42 therebetween.

The intramedullary nail 32 is a hollow nail for, e.g., receiving an adjusting means (described below with reference to FIG. 4). Further, the nail 32 has a substantially circular shape in cross section transverse to the axial (longitudinal) direction of the nail 32. For stabilizing the intramedullary nail 32 in its longitudinal direction, the shaft portion 42 and the distal end portion 40 include elongated grooves 44 extending in the longitudinal direction of the nail 32.

As also illustrated in FIGS. 2 and 3, the distal end portion 40 of the intramedullary nail 32 includes two circular transverse bores 34 and an elongated transverse bore 36 therebetween. The transverse bores 34, 36 of the distal end portion 40 are arranged along the longitudinal axis of the nail 32. Moreover, the distal end portion 40 has a tip 46 which tapers in distal direction.

As shown in FIGS. 2 and 4, the proximal end portion 38 of the intramedullary nail 32 includes a circular transverse bore 34 and an elongated transverse bore 36 which are also arranged along the longitudinal axis of the nail 32. An opening 48 is adjacent to the elongated hole 36 of the proximal end portion 38 for adjusting and fixing an adjusting means (not shown in FIG. 2) which is arranged in a hollow portion 50 within the intramedullary nail 32. A proximal end 52 of the proximal end portion 38 includes recesses 54 (slits) for receiving a holding and guiding instrument with which a surgeon can position the intramedullary nail 32 within bone.

The dummy implant system 31 further includes at least one bone screw 10 as illustrated in FIG. 1 (five are shown in FIG. 2) for anchoring the intramedullary nail 32 to bone. In principle, each of the transverse bores 34, 36 of the intramedullary nail 32 may receive a bone screw 10 as described above with reference to FIG. 1.

The front region 16 of each bone screw 10 is configured to penetrate the intramedullary nail 32 through the transverse bore 34, 36, such that the anchoring thread 20 attaches the bone screw 10 to bone. The rear region 18 having the explantation grooves 26 of bone screw 10 supports the intramedullary nail 32 at the transverse bore 34, 36. Thus, the helically arranged explantation grooves 26 facilitate the explantation of the bone screw 10 out of the transverse bore 34, 36. Specifically, the explantation grooves 26 of the rear region 18 guide, upon an explantation of the bone screw 10, the bone screw 10 inserted in the transverse bore 34, 36 out of the transverse bore 34, 36 by threadingly engaging peripheral sections of the transverse bore 34, 36.

FIG. 3 illustrates a detailed view of the distal end portion 40 of the dummy implant system 31 shown in FIG. 2. As described above, bone screws 10 are inserted in the transverse bores 34, 36 for supporting and anchoring the intramedullary nail 32 to bone. It can be further seen from FIG. 3 that the same bone screw 10 is used within the circular transverse bore 34 to fix the intramedullary nail 32 to bone and within the elongated transverse bore 36 to interact with the intramedullary nail 32 for compressing aligned bone pieces together. Consequently, bone screw 10 can be used for standard (fixation) and compression applications, such that two kinds of bone screws (one for anchoring and one for compressing) are no longer necessary. Thus, a large inventory of different bone screws is avoided in hospitals or other institutions.

FIG. 4 illustrates a cross-sectional view of the proximal end portion 38 of the dummy implant system 31 shown in FIG. 2. In a first use case, a bone screw 10 is inserted in the circular transverse bore 34 of the intramedullary nail 32. It can be seen from FIG. 4 that the rear region 18 having the helically arranged explantation grooves 26 of bone screw 10 is arranged within the circular transverse bore 34. Thus, the sidewall edges 56 of the circular transverse bore 34 abut against the rear shaft portion 18 of the bone screw 10 for supporting the nail 32. In this first case, the intramedullary nail 32 is fixedly anchored to bone.

An adjusting member 58 in form of a set screw is arranged within the hollow portion 50. The adjusting member 58 can be threadingly shifted in the axial direction of the intramedullary nail 32, such that the distal end of the adjusting member 58 extends into the elongated transverse bore 36. As shown in FIG. 4, the adjusting member 58 includes a hollow shaft portion 60 and a head portion 62 adjacent thereto. The head portion 62 of the adjusting member 58 has a recess 64 for receiving a screw driver or a wrench. Further, the head portion 62 includes an external thread 66 which mates with an internal thread 68 arranged on an internal wall of the hollow portion 50 of the proximal nail end portion 38. Thus, the adjusting member 58 can be forwarded in distal direction along the longitudinal axis of the nail 32 by turning the adjusting member 58. The position of the adjusting member 58 can be secured or fixed by a securing element (not shown in FIG. 4) inserted through the opening 48.

In a use second case, a bone screw 10 is inserted in the elongated transverse bore 36. Thus, the anchoring thread 20 of the front region 16 of bone screw 10 is anchored in bone and a portion of the rear region 18 is arranged within the elongated transverse bore 36. The adjusting member 58 is then shifted towards the distal direction by a screwing movement. As soon as the distal end of the adjusting member 58 abuts against the rear region 18 of the bone screw shaft 14, the adjusting member 58 applies a force axially of the intramedullary nail 32 to the bone screw 10. Therefore, the bone screw 10 interacts with the intramedullary nail 32, such that a compression force is applied, for example, to aligned bone pieces (not shown in FIG. 4) for holding them together. Consequently, the bone screw 10 can interact with the intramedullary nail 32 for compression applications.

Upon an explantation of the bone screw 10, the helically arranged explantation grooves 26 of rear region 18 of the bone screw shaft 14 facilitate the explantation of the bone screw 10 by threadingly engaging the sidewall edges 56 of the transverse bores 34, 36 of the nail 32, the distal end of the adjusting member 58, and/or bone. Therefore, the bone screw 10 cannot get stuck or blocked within the transverse bores 34, 36 of the intramedullary nail 32 or within the bone during an explantation process.

Since the helically arranged explantation grooves 26 of the bone screw shaft 14 are configured as described above, the bone screw 10 has a high strength (high endurance limit) for firmly anchoring the intramedullary nail 32 to bone. This strength is achieved by the optimal relation between the core diameters of the rear region 18 and the front region 16, in particular the larger core diameter of the rear region 18. Moreover, due to the configuration of the flat shaft portion 28 and the grooves 26 of the rear region 18, the bone screw 10 can provide a compression force interaction with the nail 32.

While the front region of the bone fastener has a cortical thread in the embodiment illustrated in the drawings, the thread could alternatively be configured as a spongiosa, cancellous or the like thread. Thus, the front region of the bone fastener can be adapted to different applications and may thus be threaded or even unthreaded. Moreover, while the threads as shown herein are one start threads, they could also be multiple start threads (e.g., a two-start thread).

While the head of the bone fastener as described above has an outer diameter which is greater than the outer diameter of the shaft, the head of the bone fastener can be adapted to different applications as needed and may thus have an outer diameter smaller than the diameter of the shaft or a different shape, for example, a triangle, a rectangle, a pentagon, or hexagon shape. Moreover, in some cases, a bone fastener head is not necessary at all. Therefore, the outer diameter of the proximal end of the bone fastener can equal to the outside diameter of the rear region. Further, the bone fastener and the implant described above can generally be made of stainless steel, titanium or any other biocompatible material.

While the above embodiments have exemplarily been described in relation to a bone screw and an intramedullary nail, it will be readily apparent that the techniques presents herein can also be implemented in combination with other types of bone fasteners (such as bone pegs having rod-like or pin-like shafts, wire-like bone fasteners such as Kirschner wires, etc.) as well as other types of implants (such as bone plates, bone distractors, etc.). Accordingly, the present disclosure is not limited to any type of bone fastener or any type of implant.

The features described in the above description taken in conjunction with the accompanying drawings can be readily combined to result in different embodiments. It will thus be apparent that the disclosure described above may be varied in many ways. Such variations are not to be regarded as a departure from the scope of the Such variations are not to be regarded as a departure from the scope of the invention, and all modifications are intended to be included within the scope of the following claims.

The invention claimed is:

1. A bone fastener for use in orthopaedic surgery for anchoring an intramedullary nail to bone, the bone fastener having a shaft comprising:
   a front region with an anchoring thread for attaching the bone fastener to bone, the anchoring thread has a thread pitch (b), the thread pitch (b) being defined as an axial distance between a beginning of one thread to a beginning of a next thread;
   a rear region with two or more explantation grooves helically arranged at a pitch (d), the pitch (d) being defined as an axial distance between a beginning of one groove to a beginning of a next groove substantially corresponding to the threaded pitch (b) of the anchoring thread for facilitating explantation of the bone fastener;
   wherein two axially spaced apart explantation grooves are separated by a flat shaft portion defining an outer surface having a diameter (e) of the rear region;
   wherein the two or more explantation grooves have a groove width (g) smaller than a width (h) of the flat shaft portion in an axial direction, the width (g) of the groove being the width at the outer surface of the diameter (e) of the shaft; and
   the front region and the rear region having a transition region therebetween comprising an overlap of at least one full thread between a root diameter of the anchoring thread and the outer surface of the flat shaft portion wherein the root diameter extends into the flat shaft portion.

2. The bone fastener according to claim 1, wherein the two or more explanation grooves are defined by a continuous explantation thread.

3. The bone fastener according to claim 2, wherein the explantation thread has thread peaks defining the flat shaft portion.

4. The bone fastener according to claim 2,
wherein the explanation thread in the rear region is formed as a flat, square or a trapezoidal thread.

5. The bone fastener according to claim 1,
wherein the rear region comprises multiple separate explantation grooves which are arranged in the manner of a discontinuous thread.

6. The bone fastener according to claim 1,
wherein the diameter (e) in the flat shaft portion of the rear region approximately equals an outside diameter (f) of the anchoring thread.

7. The bone fastener according to claim 1,
wherein the width (h) of the flat shaft portion is between two and four times the groove width (g) of the two or more explanation grooves in the axial direction.

8. The bone fastener according to claim 1,
wherein the two or more explantation grooves have a depth in a radial direction smaller than a thread depth of the anchoring thread.

9. The bone fastener according to claim 1,
wherein at least one of a first core diameter (a) of the shaft in the front region and a second core diameter (c) of the shaft in the rear region is constant.

10. The bone fastener according to claim 1,
wherein the anchoring thread in the front region is formed as a cortical thread or a cancellous thread.

11. A bone fastener comprising:
a head and a shaft extending therefrom;
the shaft having a first region comprising a first helical thread with a major diameter, a thread depth and a thread pitch, the thread pitch being defined as an axial distance between a beginning of one thread to a beginning of a next thread;
the shaft having a second region connected to the first region by a transition region, the second region closer to the head than the first region, the second region having a helical groove located between the head and the first region, the helical groove having a groove pitch equal to the pitch of the thread in the first region, the thread pitch in the second region being defined as an axial distance between a beginning of one groove to a beginning of a next groove, the helical groove spaced apart by a cylindrical shaft outermost surface of constant diameter equal to the major diameter, the constant diameter cylindrical shaft outer surface spacing the helical groove apart having a width wider than the width of the groove measured at the outermost surface of the cylindrical outer surface of the second region, and a length of the second region being about twice as long as a length of the first region, and the transition region comprises an overlap of at least one full thread of the first region and at least one full groove of the second region.

12. The bone fastener as set forth in claim 11 wherein the width of the cylindrical shaft surface spacing the helical groove apart is four times the width of the helical groove at the cylindrical outer surface.

13. The bone fastener as set forth in claim 11 wherein the bone fastener is a bone screw and the thread on the first region is a cortical or cancellous bone thread.

14. The bone fastener as set forth in claim 11 wherein the second region is longer than the first region in an axial direction.

15. A bone fastener for use in orthopaedic surgery for anchoring an intramedullary nail to bone, the bone fastener having a shaft comprising:
a front region extending along an axis with an anchoring thread for attaching the bone fastener to bone, wherein the anchoring thread has a thread pitch (b) and a major diameter defining an outer surface of the shaft, the thread pitch (b) being defined as an axial distance between a beginning of one thread to a beginning of a next thread;
a rear region extending along the axis connected to the front region, the rear region having a plurality of axially spaced apart separate explantation grooves spaced at a pitch (d), the pitch (d) being defined as an axial distance between a beginning of one groove to a beginning of a next groove, pitch (d) substantially corresponding to the pitch (b) of the anchoring thread for facilitating explantation of the bone fastener and having the same major diameter defining the outer surface of the shaft; and
wherein the plurality of axially spaced apart separate explanation grooves are separated by a plurality of separated flat shaft portions defining an outside diameter (e) of the rear region, and wherein a width (h) of each of the plurality of flat shaft portions at the outer surface of the shaft is at least twice the width (g) of the explantation grooves, measured at the major diameter of the shaft, in the axial direction.

16. A bone fastener for use in orthopaedic surgery for anchoring an intramedullary nail to bone, the bone fastener having a shaft comprising:
a front region having a first length with an anchoring thread for attaching the bone fastener to bone, the anchoring thread has a thread pitch (b), the thread pitch (b) being defined as an axial distance between a beginning of one thread to a beginning of a next thread;
a rear region having a second length with two or more explantation grooves arranged at a pitch (d), the pitch (d) being defined as the axial distance between the beginning of one groove to the beginning of the next groove, the pitch (d) substantially corresponding to the pitch (b) of the anchoring thread for facilitating explantation of the bone fastener;
wherein two, of the two or more explanation grooves, are separated by a flat shaft portion defining an outer surface having a diameter (e) of the rear region;
wherein the two or more explanation grooves have a groove width (g) smaller than a width (h) of the flat shaft portion in an axial direction, the width (g) of the groove being the width at the outer surface of the diameter (e) of the shaft intermediate the flat portions; and
wherein a ratio of the second length to the first length is about 2 to 1.

17. The implant system according to claim 16,
wherein the two or more explantation grooves of the rear region are configured to guide, upon an explantation of the at least one bone fastener, the at least one bone fastener inserted in the at least one transverse bore out of the at least one transverse bore.

18. The implant system according to claim 16,
wherein the intramedullary nail has at least one hollow portion and an adjusting member within said hollow portion, and the at least one transverse bore is formed as an elongated hole in the at least one hollow portion, wherein said adjusting member is configured to apply a force axially the intramedullary nail to the at least one bone fastener inserted in the elongated hole.

* * * * *